United States Patent
Uesaka et al.

(10) Patent No.: US 9,788,736 B2
(45) Date of Patent: Oct. 17, 2017

(54) BLOOD PRESSURE INFORMATION MEASUREMENT DEVICE CUFF AND BLOOD PRESSURE INFORMATION MEASUREMENT DEVICE PROVIDED THEREWITH

(75) Inventors: Chisato Uesaka, Kyoto (JP); Yukiya Sawanoi, Nara (JP)

(73) Assignee: OMRON HEALTHCARE Co., Ltd., Kyoto (JP)

(*) Notice: Subject to any disclaimer, the term of this patent is extended or adjusted under 35 U.S.C. 154(b) by 1023 days.

(21) Appl. No.: 13/592,833

(22) Filed: Aug. 23, 2012

(65) Prior Publication Data

US 2012/0316449 A1 Dec. 13, 2012

Related U.S. Application Data

(63) Continuation of application No. PCT/JP2011/052390, filed on Feb. 4, 2011.

(30) Foreign Application Priority Data

Feb. 26, 2010 (JP) .................................. 2010-043043

(51) Int. Cl.
*A61B 5/02* (2006.01)
*A61B 5/022* (2006.01)

(52) U.S. Cl.
CPC .................................. *A61B 5/02233* (2013.01)

(58) Field of Classification Search
CPC .... A61B 5/02233; A61B 17/132; A61F 5/012
USPC ....................................................... D24/165
See application file for complete search history.

(56) References Cited

U.S. PATENT DOCUMENTS

| 5,101,830 A | * | 4/1992 | Duffy et al. ................... 600/499 |
| 5,626,142 A | * | 5/1997 | Marks ............................ 600/499 |
| 6,149,600 A | | 11/2000 | Poorman-Ketchum |
| 6,645,600 B2 | * | 11/2003 | Martin ................. A44B 18/008 |
| | | | 24/451 |

(Continued)

FOREIGN PATENT DOCUMENTS

| JP | 3071616 U | 9/2000 |
| JP | 2004-166943 A | 6/2004 |

(Continued)

OTHER PUBLICATIONS

Industrial Adhesives & Tapes, copyright 2016, 3M, p. 1-3.*

(Continued)

*Primary Examiner* — Navin Natnithithadha
*Assistant Examiner* — Michael R Bloch
(74) *Attorney, Agent, or Firm* — Osha Liang LLP

(57) ABSTRACT

A cuff includes a fluid bladder, an outer cover that contains the fluid bladder toward one end portion, a surface fastener, and another surface fastener. The outer cover includes, in an area of the outer cover that includes a region in which the other surface fastener is provided, a first wide portion in which the width of the outer cover is greater than a width of an area of the outer cover that includes a region in which the surface fastener is provided. The other surface fastener includes a second wide portion in which the width of the other surface fastener is greater than the width of the surface fastener. The cuff can be fitted to a measurement area with certainty.

6 Claims, 11 Drawing Sheets

(56) References Cited

U.S. PATENT DOCUMENTS

2008/0027336 A1     1/2008   Iino et al.
2009/0043215 A1*   2/2009   Grassl ........................... 600/499

FOREIGN PATENT DOCUMENTS

| JP | 2007-275483 A | 10/2007 |
|---|---|---|
| JP | 2008-029684 A | 2/2008 |
| WO | 97/18750 A1 | 5/1997 |
| WO | 2007/119482 A1 | 10/2007 |

OTHER PUBLICATIONS

Scotchmate™ Hook & Loop Fastening System, updated Jul. 1999, 3M, p. 1-4.*
Hook and loop fastener, Wikipedia, retrieved Dec. 26, 2016, p. 1-5.*
Velcro, copyright 1999 retrieved Dec. 26, 2016, EDinformatics, p. 1-2.*
Office Action issued Dec. 22, 2014 in related Russian Patent Application No. 2012141056/14(066183) (9 pages) (with translation).
International Search Report issued in corresponding International Application No. PCT/JP2011/052390 dated Mar. 1, 2011 and English translation thereof (2 pages).
Patent Abstracts of Japan, Publication No. 2004-166943, Published on Jun. 17, 2004, 1 page.
Patent Abstracts of Japan, Publication No. 2007-275483, Published on Oct. 25, 2007, 1 page.
Patent Abstracts of Japan, Publication No. 2008-029684, Published on Feb. 14, 2008, 1 page.

* cited by examiner

BLOOD PRESSURE INFORMATION MEASUREMENT DEVICE CUFF AND BLOOD PRESSURE INFORMATION MEASUREMENT DEVICE PROVIDED THEREWITH

TECHNICAL FIELD

The present invention relates to blood pressure information measurement device cuffs that are used while being worn on a measurement area when measuring blood pressure information such as a blood pressure value, and to blood pressure information measurement devices provided with such cuffs.

BACKGROUND ART

Blood pressure information measurement devices obtain blood pressure information of a measurement subject. The blood pressure information obtained by such blood pressure information measurement devices includes various types of information related to the circulatory system of the measurement subject, such as a systolic blood pressure value (a maximum blood pressure value), a diastolic blood pressure value (a minimum blood pressure value), an average blood pressure value, a sphygmogram, pulse, AI (Augmentation Index) value, and the like of the measurement subject, and so on. Stress on the heart of the measurement subject, changes in the hardness of arteries of the measurement subject, or the like can be understood based on this blood pressure information. A blood pressure information measurement device is used in the early detection, prevention, treatment, and so on of a measurement subject's circulatory system conditions.

Generally speaking, a blood pressure information measurement device cuff (called simply a "cuff" hereinafter) is used in the measurement of blood pressure information. The cuff is a band-shaped member having an inner cavity, and is wrapped around a part of a body such as an upper arm. The cuff contains a fluid bladder for pressurizing the body (an artery).

In a blood pressure information measurement device used to measure blood pressure values such as a systolic blood pressure value or a diastolic blood pressure value (called simply a "sphygmomanometer" hereinafter), the cuff is wrapped around the surface of part of the body, and a fluid such as air, a liquid, or the like is injected into and exhausted from the fluid bladder contained in the cuff. The fluid bladder inflates and deflates when the fluid is injected or exhausted, and a change in the inner pressure of the fluid bladder produced at this time is obtained as an arterial pulse wave or a blood pressure value.

FIG. 14 is a plan view illustrating a typical cuff 100A in an unrolled state. In FIG. 14, part of an outer cover 30 is illustrated in a broken manner, but in reality, the outer cover 30 continues through that part. The same applies to FIG. 15, described later.

Referring to FIG. 14, the cuff 100A includes the outer cover 30, an air bladder (not shown) contained as a fluid bladder within the outer cover 30, a surface fastener 41, and a surface fastener 42.

The outer cover 30, meanwhile, has a front surface 31, a rear surface 32, one end portion 30a, another end portion 30b, one side portion 30c, and another side portion 30d.

The air bladder is connected to an air tube 80 while being contained within the outer cover 30. The air bladder is provided toward the one end portion 30a in the lengthwise direction of the outer cover 30. The "lengthwise direction" mentioned here refers to the direction that connects the one end portion 30a and the other end portion 30b of the outer cover 30.

The surface fastener 41 is provided upon the front surface 31 of the outer cover 30. The surface fastener 42 is provided upon the rear surface 32 of the outer cover 30. The surface fastener 41 and the surface fastener 42 are capable of interlocking with each other.

The cuff 100A is worn so that the rear surface 32 of the outer cover 30 and the body (not shown) are opposed to each other (see FIG. 16). The cuff 100A is wrapped around the body in a ring shape. Fastening the surface fastener 41 and the surface fastener 42 to each other holds the outer cover 30, which has been wrapped into a ring shape, on the body in a secured state. The air bladder contained within the outer cover 30 is thus anchored to the body, and the blood pressure information can then be measured. A cuff having essentially the same configuration as the cuff 100A is disclosed in JP 2004-166943A (Patent Literature 1), below.

Another form of the outer cover 30 will be described with reference to FIG. 15. As exemplified by the outer cover 30 of a cuff 100B, some configurations have the outer cover 30 gradually becoming narrower as the outer cover 30 progresses from the one end portion 30a to the other end portion 30b. Although the outer cover 30 of the cuff 100B is configured so that the outer cover 30 narrows only on the side portion 30d, there are also configurations in which the outer cover 30 narrows on both the side portion 30c and the side portion 30d.

Referring to FIG. 16, there are cases where, when the cuff 100A is, for example, wrapped around an upper arm 70, the cuff 100A is fastened with the other end portion 30b of the outer cover 30 shifted toward the shoulder. The side portion 30c of the outer cover 30 in the vicinity of the other end portion 30b is disposed protruding from the front surface 31 of the outer cover 30 (on the side of the one end portion 30a) that has already been wrapped, toward the outer side (that is, the surface of the upper arm 70). The greater the difference between a length H1 around the upper arm 70 near the shoulder and a length H2 around the upper arm 70 near the elbow is, the greater the shift toward the shoulder will be when the other end portion 30b of the outer cover 30 is fastened.

In this case, the contact surface area is low between the surface fastener 41 and the surface fastener 42, and thus the surface fastener 41 and the surface fastener 42 have a low fastening force. The air bladder therefore cannot be inflated or deflated to the desired pressure, and this can also cause the cuff 100A to separate from the upper arm 70 while measuring the blood pressure value. As a result, variations occur in the measured values, which makes it difficult to measure the blood pressure information in an accurate and stable manner. Likewise, when the cuff 100B shown in FIG. 15 is, for example, wrapped around the upper arm 70, the contact surface area between the surface fastener 41 and the surface fastener 42 drops, variations in the measured values occurs, and it becomes difficult to measure the blood pressure information in an accurate and stable manner.

Referring to FIG. 17, there are also cases where when the cuff 100A is wrapped around the upper arm 70, the cuff 100A is wrapped so that the surface fastener 42 visibly overlaps with the surface fastener 41. To rephrase, the side portion 30c of the outer cover 30 near the other end portion 30b is disposed so as to overlap with the side portion 30c of the outer cover 30 that is already wrapped around the upper arm 70 (that is, on the side of the one end portion 30a).

Likewise, the side portion 30d of the outer cover 30 near the other end portion 30b is disposed so as to overlap with the side portion 30d of the outer cover 30 that is already wrapped around the upper arm 70 (that is, on the side of the one end portion 30a).

In this case, a greater difference between the aforementioned length H1 in the aforementioned length H2 results in an insufficient length on the side of the side portion 30d of the outer cover 30 (that is, the side closer to the elbow) and an excessive length on the side of the side portion 30c of the outer cover 30 (that is, the side closer to the shoulder), and thus a gap S is formed between the surface fastener 41 and the surface fastener 42.

Due to the gap S, the contact surface area between the surface fastener 41 and the surface fastener 42 decreases, and thus the fastening force between the surface fastener 41 and the surface fastener 42 is reduced. The air bladder therefore cannot be inflated and deflated to the desired pressure, and this can also cause the cuff 100A to separate from the upper arm 70 while measuring the blood pressure value. As a result, variations occur in the measured values, which makes it difficult to measure the blood pressure information in an accurate and stable manner.

Patent Literature 1: JP 2004-166943A

SUMMARY OF INVENTION

One or more embodiments of the present invention provide a blood pressure information measurement device cuff capable of being fitted to a measurement area with certainty, and to provide a blood pressure information measurement device including such a blood pressure information measurement device cuff.

A blood pressure information measurement device cuff according to one or more embodiments of the present invention includes: a fluid bladder that applies pressure to a body; an outer cover, having a first main surface and a second main surface, that contains the fluid bladder toward one end portion; a first fastening member provided toward the one end portion on the first main surface; and a second fastening member provided toward another end portion on the first main surface or toward the other end portion on the second main surface. The outer cover is wrapped around the body in a ring shape; the first fastening member and the second fastening member hold the wrapped outer cover on the body in a secured state; the outer cover includes, in an area of the outer cover that includes a region in which the second fastening member is provided, a first wide portion in which the width of the outer cover is greater than a width of an area of the outer cover that includes a region in which the first fastening member is provided; and the second fastening member includes a second wide portion in which the width of the second fastening member is greater than a width of the first fastening member.

According to one or more embodiments of the present invention, the first wide portion in the outer cover and the second wide portion in the second fastening member have approximately arc shapes in which the widths gradually increase outward in the width direction as the outer cover progresses from the one end portion toward the other end portion.

According to one or more embodiments of the present invention, the first wide portion in the outer cover and the second wide portion in the second fastening member have shapes in which the widths increase outward on both sides in the width direction as the outer cover progresses from the one end portion toward the other end portion.

According to one or more embodiments of the present invention, the first wide portion in the outer cover and the second wide portion in the second fastening member can be bent toward the first main surface or the second main surface.

According to one or more embodiments of the present invention, openings that pass through from the first main surface to the second main surface are provided in the second fastening member and in the area of the outer cover that includes the region in which the second fastening member is provided, respectively.

A blood pressure information measurement device cuff according to one or more embodiments of the present invention includes: a fluid bladder that applies pressure to a body; a first outer cover that contains the fluid bladder; a first fastening member provided in the first outer cover; a second outer cover; a second fastening member provided in the second outer cover; and a connecting member that connects another end portion of the first outer cover to one end portion of the second outer cover in a pivotable state, wherein the first outer cover and the second outer cover are wrapped around the body in a ring shape while being connected to each other by the connecting member; and the first fastening member and the second fastening member hold the wrapped first outer cover and second outer cover on the body in a secured state.

A blood pressure information measurement device according to one or more embodiments of the present invention includes one of the stated blood pressure information measurement device cuffs, an inflation/deflation mechanism that inflates/deflates the fluid bladder, and a blood pressure information obtainment unit that obtains blood pressure information.

According to one or more embodiments of the present invention, it is possible to obtain a blood pressure information measurement device cuff capable of being fitted to a measurement area with certainty, and a blood pressure information measurement device provided with such a cuff.

DETAILED DESCRIPTION OF INVENTION

Figure 1:
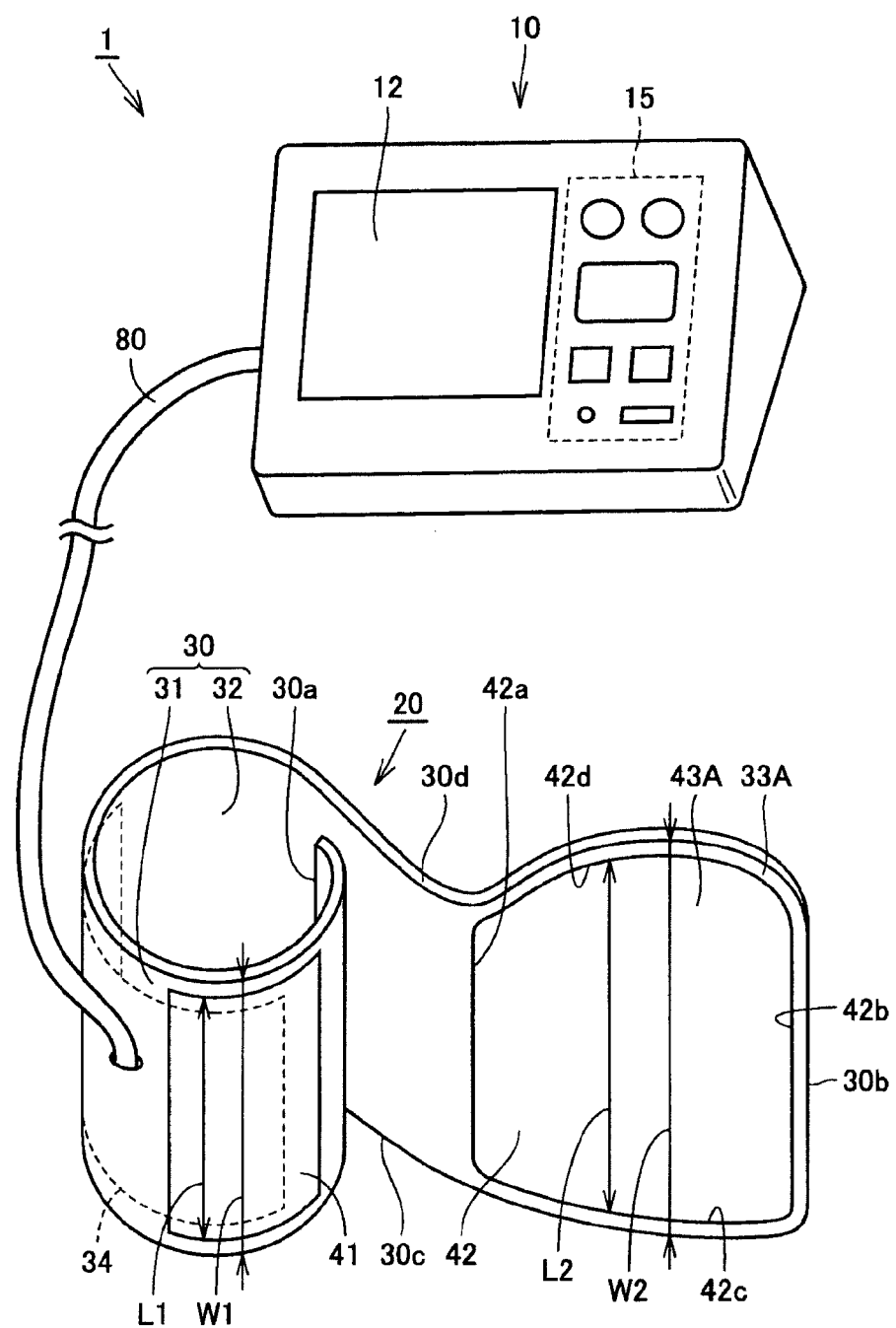
FIG. 1 is a diagram illustrating the overall configuration of a sphygmomanometer according to a first embodiment.

A blood pressure information measurement device cuff and a blood pressure information measurement device provided therewith according to one or more embodiments of the present invention will be described hereinafter with reference to the drawings.

In the following embodiments, a sphygmomanometer cuff that is used by being wrapped around an upper arm will be described as an example of the blood pressure information measurement device cuff. A sphygmomanometer capable of measuring blood pressure values such as a systolic blood pressure value and a diastolic blood pressure value using the sphygmomanometer cuff will be described as an example of the blood pressure information measurement device provided with the blood pressure information measurement device cuff.

When numbers, amounts, and so on are discussed in the following embodiment, it should be noted that unless explicitly mentioned otherwise, the scope of the present invention is not necessarily limited to those numbers, amounts, and so on. In the embodiment described hereinafter, identical and corresponding components may be assigned identical reference numerals, and redundant descriptions thereof may be omitted.

First Embodiment

A sphygmomanometer 1 according to the present embodiment will be described with reference to FIGS. 1 through 4.

Configuration of Sphygmomanometer 1

As shown in FIG. 1, the sphygmomanometer 1 includes a main body 10, a cuff 20, and an air tube 80. The main body 10 includes a box-shaped housing. A display unit 12 and an operating unit 15 are provided in the top surface of the main body 10. During measurement, the main body 10 is used by being placed on a table or the like.

The cuff 20 includes: an outer cover 30; an air bladder 34 contained in the outer cover 30 as a fluid bladder; a surface fastener 41 (a first fastening member), and a surface fastener 42 (a second fastening member).

The outer cover 30, meanwhile, has a front surface (first main surface) 31, a rear surface (second main surface) 32, one end portion 30a, another end portion 30b, one side portion 30c, and another side portion 30d. The outer cover 30 is configured as a bladder-shaped member in which a member that configures the front surface 31 and a member that configures the rear surface 32 are overlapped and the outer edges thereof are connected (for example, stitched, welded, or the like) together. The cuff 20 is disposed so that the rear surface 32 of the outer cover 30 and a body such as an upper arm are opposed to each other.

According to one or more embodiments of the present invention, a member that is sufficiently capable of stretching is used as the member that configures the rear surface 32 side of the outer cover 30 so that the pressurizing force applied to the upper arm by the inflation of the air bladder 34 is not inhibited.

A member that is less capable of stretching than the member of which the rear surface 32 side of the outer cover 30 is configured is used as the member that configures the front surface 31 side of the outer cover 30. Thus a material configured of synthetic fibers such as polyamide (PA), polyester, or the like, the stretchability of which can be adjusted relatively easily, is used as the member that configures the front surface 31 side of the outer cover 30.

The air bladder 34 is connected to the air tube 80. The air bladder 34 is contained within the one end portion 30a in the lengthwise direction of the outer cover 30. The air bladder 34 is configured of a bag-shaped member, and has, in its interior, a space that can inflate and deflate. According to one or more embodiments of the present invention, the air bladder 34 is configured using resin sheets. The air bladder 34 can be formed in a bag shape by, for example, overlaying two resin sheets and welding the edges thereof to each other.

Any material can be used for the resin sheets that configure the air bladder 34 as long as the material is stretchable and there are no leaks from the inflating/deflating space after the welding has been carried out. According to one or more embodiments of the present invention, the material for the resin sheets that configure the air bladder 34 is, for example, ethylene-vinyl acetate copolymer (EVA), soft polyvinyl chloride (PVC), polyurethane (PU), natural rubber (NR), or the like.

The air tube 80 connects the main body 10 and the air bladder 34 contained within the cuff 20, which are configured as separate entities. The air bladder 34 inflates as a result of a fluid being injected thereinto from the main body 10 through the air tube 80. The air bladder 34 shrinks deflates as a result of the fluid being exhausted therefrom from the main body 10 through the air tube 80. As a result of this inflation and deflation, the air bladder 34 can apply pressure to a body such as the upper arm.

There are cases where a curler (not shown), configured as a curved elastic plate, is contained within the outer cover 30 in addition to the air bladder 34. The curler is typically configured of a flexible, approximately cylindrical member so as to fit to the body. The curler is partially split in the axial direction thereof, and is contained within the outer cover 30 so as to follow the lengthwise direction of the outer cover 30. As a result, the curler can elastically deform in the radial direction when wrapped around the body. The curler is disposed on the outside of the air bladder 34 (that is, the outside of the air bladder 34 when the cuff 20 is wrapped around the body).

Details of Outer Cover 30 and Surface Fasteners 41, 42

Figure 2:
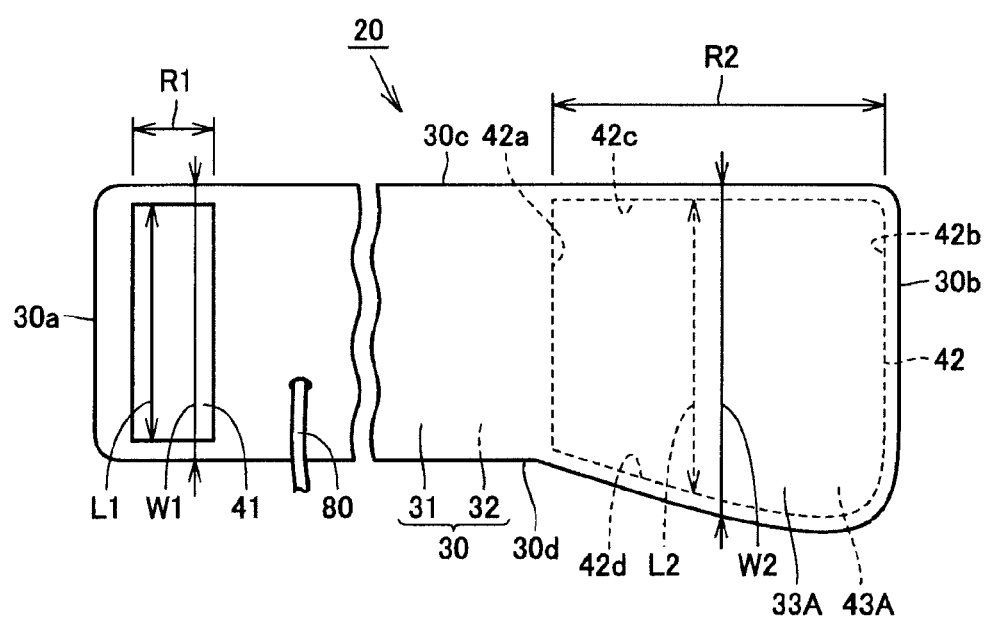
FIG. 2 is a plan view illustrating a cuff according to the first embodiment.

FIG. 2 is a plan view illustrating the cuff 20 used in the sphygmomanometer 1 according to the present embodiment in an unrolled state.

In FIG. 2, the air bladder 34 contained within the outer cover 30 is not shown. The same applies to FIGS. 5 through 12, referred to in the descriptions of the first variation through seventh variation of the first embodiment and the second embodiment, which follow later.

In FIG. 2, part of the outer cover 30 is illustrated in a broken manner, but in reality, the outer cover 30 continues through that part. The same applies to FIGS. 5 through 12.

As shown in FIG. 2, the one side portion 30c of the outer cover 30 is configured in an approximately linear shape following the lengthwise direction. Of the outer cover 30, an area including a region R1 in which the surface fastener 41 is provided is configured as an approximate band-shape that extends in the lengthwise direction. This area has a width W1.

In the outer cover 30, only the other side portion 30d is configured so as to curve outward (downward, in the drawings) and widen. The other side portion 30d of the outer cover 30 is configured so that the width of the outer cover 30 gradually increases in an area of the outer cover 30 that includes a region R2 in which the surface fastener 42 is provided, as the outer cover 30 progresses from the one end portion 30a toward the other end portion 30b. Continuing from this configuration, the other side portion 30d of the outer cover 30 is configured so that the width of the outer cover 30 drops comparatively suddenly as the outer cover 30 progresses from the one end portion 30a toward the other end portion 30b.

Of the outer cover 30, the area including the region R2 in which the surface fastener 42 is provided has, in a part thereof, a width W2.

The width W2 of part of the area including the region R2 in which the surface fastener 42 is provided is set to be greater than the width W1 of the area of the outer cover 30 including the region R1 in which the surface fastener 41 is provided. In the area of the outer cover 30 that is set to be wider, the outer cover 30 has a first wide portion 33A that protrudes toward the other side portion 30d.

The surface fastener 41 is provided upon the front surface 31 of the outer cover 30 in an approximately rectangular shape. The surface fastener 41 is provided toward the one end portion 30a of the outer cover 30. The surface fastener 41 is provided in approximately the central position of the width direction of the outer cover 30. The surface fastener 41 has a width L1.

The surface fastener 42 is provided upon the rear surface 32 of the outer cover 30. The surface fastener 42 is provided toward the other end portion 30b of the outer cover 30. The surface fastener 42 has one end portion 42a, another end portion 42b, one side portion 42c, and another side portion 42d.

The one side portion 42c of the surface fastener 42 is configured in a linear shape that is approximately parallel to the lengthwise direction of the outer cover 30.

In the surface fastener 42, only the other side portion 42d is configured so as to curve outward (downward, in the drawings) and widen. The other side portion 42d of the surface fastener 42 is configured so that the width of the surface fastener 42 gradually increases as the surface fastener 42 progresses from the one end portion 42a toward the other end portion 42b. The other side portion 42d of the surface fastener 42 is configured so that the width of the surface fastener 42 drops comparatively suddenly near the other end portion 42b, as the surface fastener 42 progresses from the one end portion 42a toward the other end portion 42b. The surface fastener 42 has a width L2 in a part thereof.

The width L2 in a part of the surface fastener 42 is set to be greater than the width L1 of the surface fastener 41. In the area of the surface fastener 42 that is set to be wider, the surface fastener 42 has a second wide portion 43A that protrudes toward the other side portion 42d.

When measuring a blood pressure value using the sphygmomanometer 1 having the stated configuration, the cuff 20 is positioned so that the rear surface 32 of the outer cover 30 opposes, for example, an upper arm.

The outer cover 30 is wrapped around the upper arm in a ring shape so that the approximate center position of the air bladder 34 in the lengthwise direction thereof (see FIG. 1) opposes a measurement area. The surface fastener 41 and the surface fastener 42 are fastened to each other by overlapping, thus holding the wrapped outer cover 30 on the body in a secured state. The air bladder contained within the outer cover 30 is thus anchored to the body, and the blood pressure information can then be measured.

Functional Blocks of Sphygmomanometer 1

Figure 3:
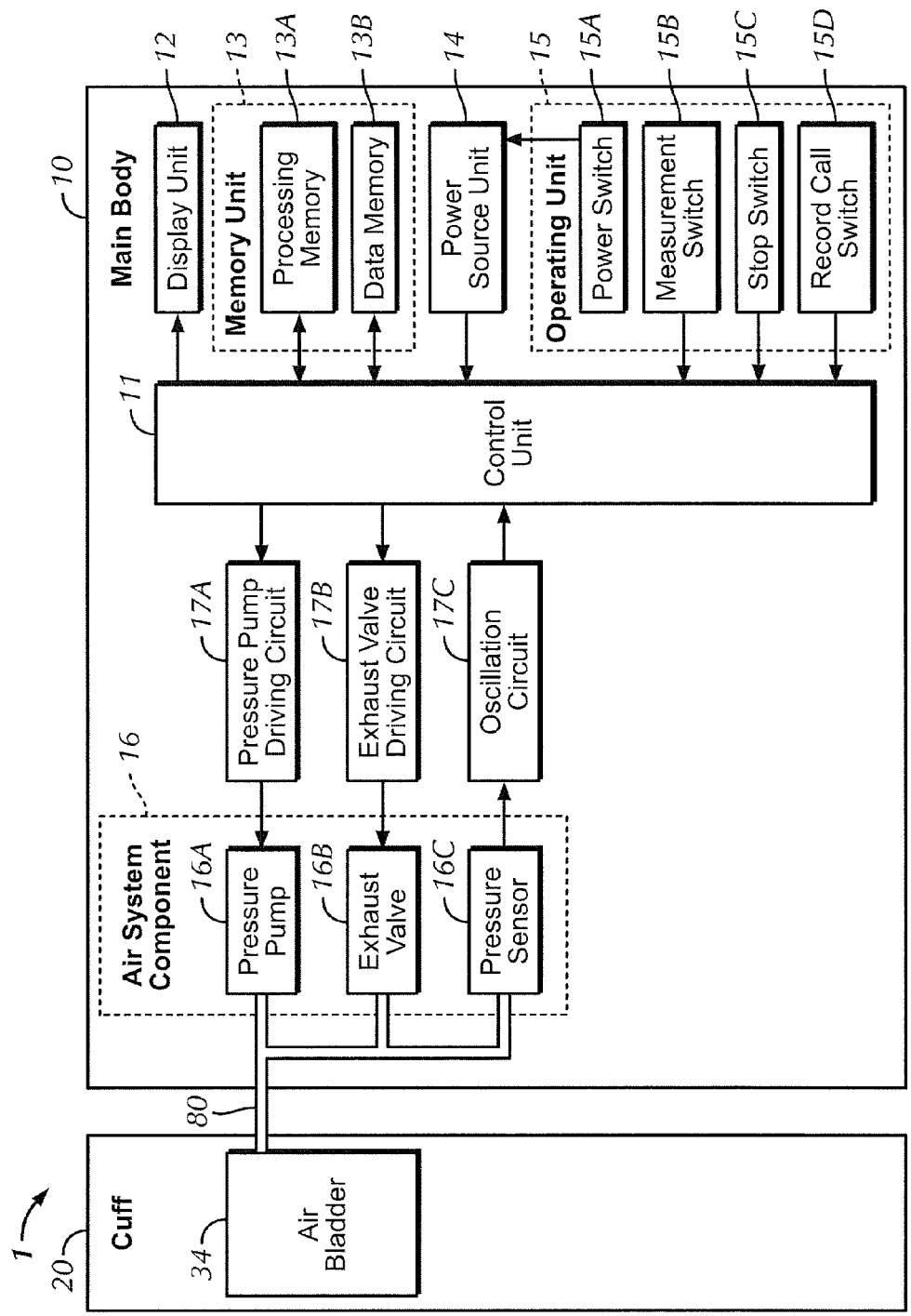
FIG. 3 is a function block diagram illustrating the sphygmomanometer according to the first embodiment.

The functional blocks of the sphygmomanometer 1 will be described with reference to FIG. 3. The main body 10 of the sphygmomanometer 1 includes, in addition to the aforementioned display unit 12 and operating unit 15, a control unit 11, a memory unit 13, a power source unit 14, a pressure pump 16a, an exhaust valve 16b, a pressure sensor 16c, a pressure pump driving circuit 17a, an exhaust valve driving circuit 17b, and an oscillation circuit 17c.

The pressure pump 16a, exhaust valve 16b, and pressure sensor 16c correspond to an air system component 16 of the sphygmomanometer 1. The pressure pump 16a and exhaust valve 16b correspond to an inflation/deflation mechanism in the sphygmomanometer 1 for inflating and deflating the air bladder 34.

The air bladder 34 has an inflation/deflation space, serving as a cavity, in its interior, as described above. The air bladder 34 is connected to the pressure pump 16a, the exhaust valve 16b, and the pressure sensor 16c, respectively, via the air tube 80.

The control unit 11 is configured of, for example, a CPU (central processing unit). The control unit 11 controls the sphygmomanometer 1 as a whole. The display unit 12 is configured of, for example, an LCD (liquid-crystal display). The display unit 12 displays measurement results and the like.

The memory unit 13 is configured of a processing memory 13a and a data memory 13b. Using the processing memory 13a and the data memory 13b, the memory unit 13 stores programs for causing the control unit 11 to carry out processes for blood pressure value measurement, stores measurement results and the like, and so on.

The power source unit 14 supplies electricity, as a power source, to the control unit 11. The operating unit 15 is configured of a power switch 15a, a measurement switch 15b, a stop switch 15c, and a record call switch 15d. The operating unit 15 accepts operations of the switches 15a through 15d from a measurement subject or the like, and inputs commands from the exterior into the control unit 11 or the power source unit 14.

The control unit 11 inputs control signals for driving the pressure pump 16a and the exhaust valve 16b into the pressure pump driving circuit 17a and the exhaust valve driving circuit 17b, respectively. The control unit 11 inputs a blood pressure value, serving as a measurement result, into the memory unit 13 or the display unit 12.

The control unit 11 includes a blood pressure information obtainment unit (not shown) that obtains a blood pressure value of the measurement subject based on a pressure value detected by the pressure sensor 16c. The blood pressure value obtained by the blood pressure information obtainment unit is inputted into the aforementioned memory unit 13 or the display unit 12 as a measurement result.

The sphygmomanometer 1 may also include a separate output unit that outputs a blood pressure value to an external device (for example, a PC (personal computer), a printer, or the like) as the measurement result. For example, a serial communication line, a device that writes to various types of recording media, or the like can be used as the output unit.

The inflation/deflation operations performed by the pressure pump 16a are controlled by the pressure pump driving circuit 17a based on the control signal inputted from the control unit 11. The pressure pump 16a increases the pressure within the air bladder 34 (this will be called a "cuff pressure" hereinafter) by supplying a fluid such as air to the inner cavity of the air bladder 34.

The opening/closing operations of the exhaust valve 16b are controlled by the exhaust valve driving circuit 17b based on the control signal inputted from the control unit 11. The exhaust valve 16b maintains the pressure within the air bladder 34, decreases the cuff pressure by opening the inner cavity of the air bladder 34 to the exterior, and so on.

The pressure sensor 16c inputs, to the oscillation circuit 17c, an output signal based on the pressure within the air bladder 34. The oscillation circuit 17c generates an oscillation frequency signal in accordance with the signal inputted from the pressure sensor 16c, and inputs the generated signal to the control unit 11.

Flow of Processing of Sphygmomanometer 1

Figure 4:
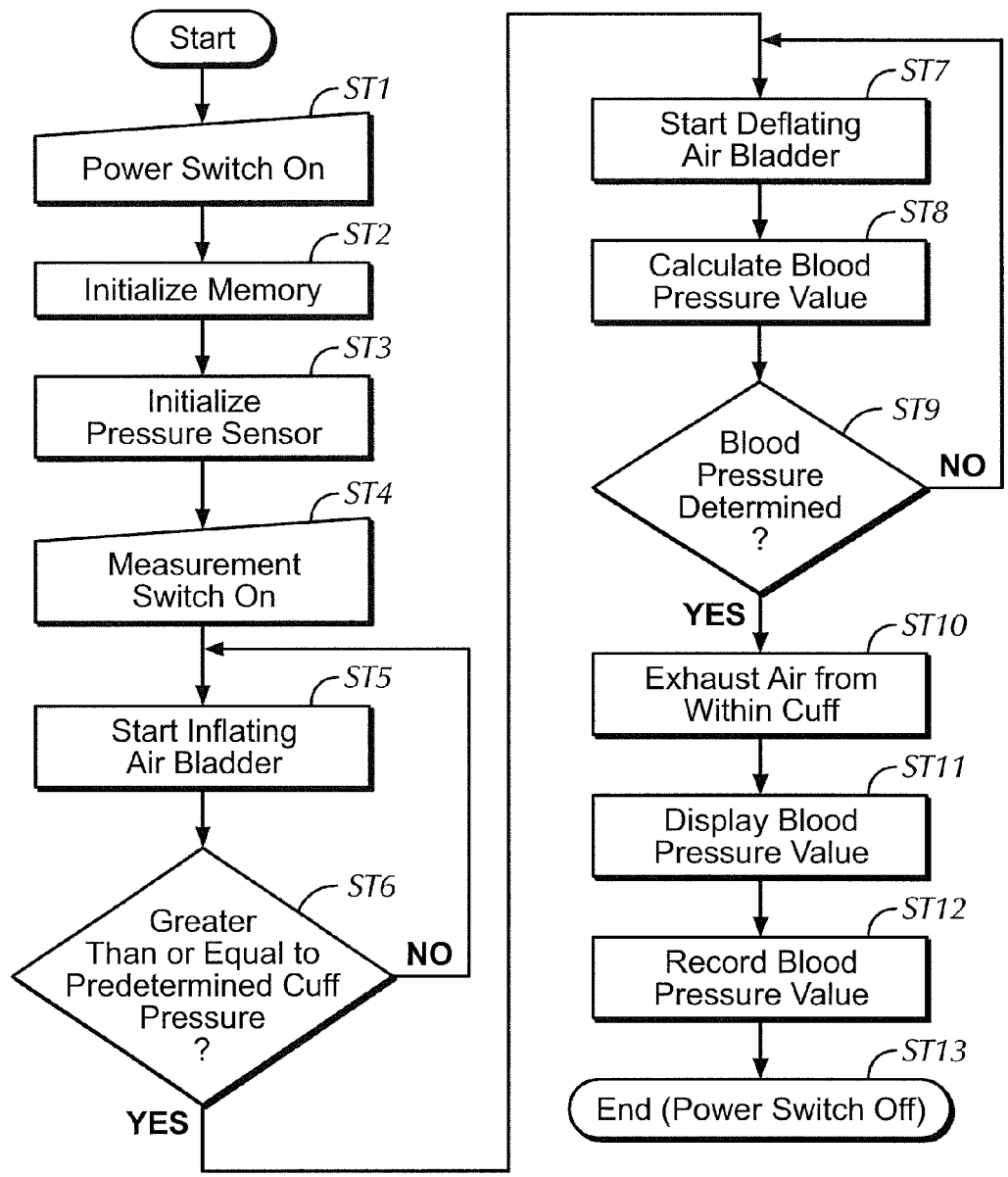
FIG. 4 is a diagram illustrating the flow of processing performed by the sphygmomanometer according to the first embodiment.

A flow of processing performed by the sphygmomanometer 1 will be described with reference to FIG. 3 and FIG. 4. A program that follows the flow of the processing performed by the sphygmomanometer 1 is stored in advance in the memory unit 13. The processing of the sphygmomanometer 1 is executed by the control unit 11 reading out this program from the memory unit 13 and executing the program.

When measuring a blood pressure value, the measurement subject first attaches the cuff 20 to his or her upper arm. In this state, the measurement subject manipulates the operating unit 15 (the power switch 15a) provided in the main body 10, and turns the sphygmomanometer 1 on (step ST1).

Electricity, serving as a power source, is supplied from the power source unit 14 to the control unit 11, thus driving the control unit 11. The control unit 11 then initializes the memory unit 13 (step ST2). Next, the control unit 11 initializes the pressure sensor 16c (step ST3).

The control unit 11 then stands by for an instruction to start the measurement from the measurement subject. As an instruction to start the measurement, the measurement subject manipulates the operating unit 15 (the measurement switch 15b) (step ST4). The control unit 11 closes the exhaust valve 16b and drives the pressure pump 16a. The inflation of the air bladder 34 is started (step ST5).

The cuff pressure in the air bladder 34 rises. The cuff pressure in the air bladder 34 then becomes greater than or equal to a predetermined cuff pressure required for blood pressure value measurement (step ST6). The control unit 11 then stops the pressure pump 16a and opens the exhaust valve 16b that was closed. The air within the air bladder 34 is exhausted, and the air bladder 34 gradually begins to deflate (step ST7).

With the sphygmomanometer 1 according to the present embodiment, the blood pressure value is measured while the cuff pressure is gradually decreasing. The sphygmomanometer 1 calculates a blood pressure value, such as a systolic blood pressure value, a diastolic blood pressure value, or the like, using the control unit 11 (step ST8).

The control unit 11 extracts sphygmogram information based on an oscillation frequency obtained from the oscillation circuit 17c while the cuff pressure of the air bladder 34 is gradually decreasing. The control unit 11 determines the blood pressure value based on the extracted sphygmogram information (step ST9).

When the blood pressure value is determined, the control unit 11 opens the exhaust valve 16b and completely exhausts the air from within the air bladder 34 (step ST10). The control unit 11 then displays the blood pressure value, serving as a measurement result, in the display unit 12 (step ST11). The control unit 11 then stores the blood pressure value in the memory unit 13, and records that value as data (step ST12).

The measurement subject and then operates the operating unit 15 (the power switch 15a) provided in the main body 10, and turns the sphygmomanometer 1 off. Turning the sphygmomanometer 1 off ends the operations thereof (step ST13).

The measurement method described thus far is what is known as a deflation measurement method, which detects a sphygmogram while the air bladder 34 is deflating. However, the measurement method for the sphygmomanometer 1 according to the present embodiment is not limited to the deflation measurement method, and what is known as an inflation measurement method, which detects a sphygmogram while the air bladder 34 is inflating, can also be employed.

Effects

As shown in FIG. 1, the cuff 20 is worn so that the rear surface 32 of the outer cover 30 is opposed to the body, such as the upper-left arm (not shown) of the measurement subject. Using his or her right hand, the measurement subject wraps the cuff 20 around the upper arm in a ring shape so that the approximate center position of the air bladder 34 in the lengthwise direction opposes the measurement area.

When the cuff 20 is wrapped around the upper arm in a ring shape, the one end portion 30a of the outer cover 30 is sandwiched between the upper arm and the rear surface 32 of the outer cover 30. The outer cover 30 is then secured to the upper arm. By being fastened to each other, the surface fastener 41 and the surface fastener 42 maintain a state in which the wrapped outer cover 30 is secured to the upper arm. The air bladder 34 contained within the outer cover 30 is thus anchored to the upper arm, and the blood pressure information can then be measured.

In the sphygmomanometer 1 according to the present embodiment, the first wide portion 33A is provided in the outer cover 30, and the second wide portion 43A is provided in the surface fastener 42. In addition, in the sphygmomanometer 1 according to the present embodiment, the side portion on which the first wide portion 33A and the second wide portion 43A are provided (the other side portion 30d) is disposed so as to be positioned toward the elbow (see FIG. 16).

When the cuff 20 is wrapped around a body such as the upper arm, there are cases where the cuff 20 is fastened in a state where the side portion 30c in the other end portion 30b of the outer cover 30 is shifted toward the shoulder. As described at the beginning with reference to FIG. 16, a portion of the surface fastener 41 that does not make contact with the surface fastener 42 and is therefore exposed is, according to the sphygmomanometer 1 in the present embodiment, covered by the second wide portion 43A.

The surface fastener 41 and the surface fastener 42 make contact with each other with a sufficient contact surface area. By increasing the contact surface area between the surface fastener 41 and the surface fastener 42, it is possible to ensure a sufficient fastening force between the surface fastener 41 and the surface fastener 42.

The air bladder 34 can then be inflated and deflated to the desired pressure, which makes it possible to prevent the cuff 20 from falling off the body, such as the upper arm, while the blood pressure value is being measured. Therefore, according to the cuff 20 and the sphygmomanometer 1 provided therewith in the present embodiment, the cuff can be affixed to the measurement area with certainty, eliminating variations in the measurement values, which makes it possible to measure the blood pressure information in an accurate and stable manner.

First Variation

Figure 5:
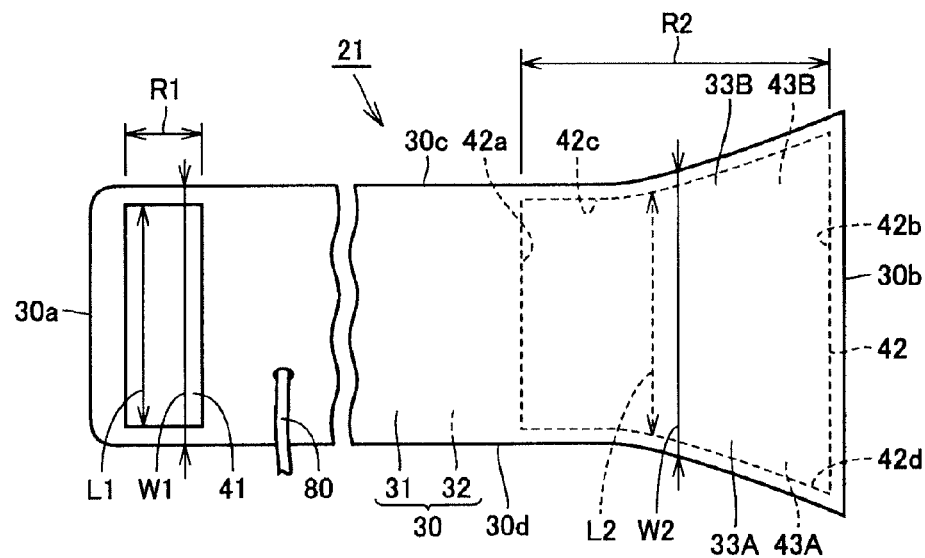
FIG. 5 is a plan view illustrating a cuff according to a first variation on the first embodiment.

A sphygmomanometer according to a first variation on the first embodiment will be described with reference to FIG. 5. In the present variation, only the differences from the first embodiment will be described. The first embodiment and the present variation differ in that the cuff has a different configuration; the other configurations are essentially the same.

To be more specific, the first embodiment and the present variation differ in terms of the external shape of the outer cover 30 that partially configures a cuff 21 (see FIG. 5) and the external shape of the surface fastener 42 that partially configures the cuff 21.

In the present variation, of the outer cover 30, an area including the region R1 in which the surface fastener 41 is provided is configured as an approximate band-shape that extends in the lengthwise direction, in the same manner as in the first embodiment. This area has a width W1.

In the present variation, of the outer cover 30, an area including the region R2 in which the surface fastener 42 is provided is configured so that, in addition to the other side portion 30d, the one side portion 30c also widens toward the outside (upward, in the drawings).

In an area of the outer cover 30 including the region R2 in which the surface fastener 42 is provided, the one side portion 30c of the outer cover 30 is configured having an arc shape in which the width of the outer cover 30 gradually increases (upward, in the drawings), as the outer cover 30 progresses from the one end portion 30a toward the other end portion 30b.

In the area of the outer cover 30 including the region R2 in which the surface fastener 42 is provided, the other side portion 30d of the outer cover 30 is configured having an arc shape in which the width of the outer cover 30 gradually increases (downward, in the drawings), as the outer cover 30 progresses from the one end portion 30a toward the other end portion 30b.

Of the outer cover 30, the area including the region R2 in which the surface fastener 42 is provided has, in a part thereof, a width W2.

The width W2 of part of the area including the region R2 in which the surface fastener 42 is provided is, as in the first embodiment, set to be greater than the width W1 of the area of the outer cover 30 including the region R1. In the area of the outer cover 30 that is set to be wider, the outer cover 30 has, in addition to the first wide portion 33A that protrudes toward the other side portion 30d, another first wide portion 33B that protrudes toward the one side portion 30c.

In the present variation, the surface fastener 42 is configured so that, in addition to the other side portion 42d, the one side portion 42c also widens toward the outside (upward, in the drawings). The one side portion 42c of the surface fastener 42 is configured having an arc shape so that the width of the surface fastener 42 gradually increases as the surface fastener 42 progresses from the one end portion 42a toward the other end portion 42b. The surface fastener 42 has a width L2 in a part thereof.

The width L2 in a part of the surface fastener 42 is, as in the first embodiment, set to be greater than the width L1 of the surface fastener 41. In the area of the surface fastener 42 that is set to be wider, the surface fastener 42 has, in addition to the second wide portion 43A that protrudes toward the other side portion 42d, another second wide portion 43B that protrudes toward the one side portion 42c.

Effects

With the cuff 21 according to the present variation, the outer cover 30 includes the first wide portion 33A and the other first wide portion 33B, and the surface fastener 42 includes the second wide portion 43A and the other second wide portion 43B.

According to the first embodiment, it is necessary for the cuff 20 to be wrapped so that the side on which the first wide portion 33A and the second wide portion 43A are provided (that is, the side portion 30d side of the outer cover 30) is positioned toward the elbow, in order to bring the surface fastener 41 and the surface fastener 42 into sufficient contact with each other. Therefore, a sphygmomanometer provided with the cuff 20 according to the first embodiment can be wrapped and used on only one arm (for example, the left arm).

However, with the outer cover 30 according to the present variation, the first wide portion 33A and the second wide portion 43A are provided on the side portion 30d side of the outer cover 30, and the other first wide portion 33B and other second wide portion 43B are provided on the side portion 30c side of the outer cover 30. Therefore, a sphygmomanometer provided with the cuff 21 according to the present variation can be wrapped and used on either arm (the right arm or the left arm).

The first wide portions 33A and 33B in the outer cover 30 and the second wide portions 43A and 43B in the surface fastener 42 are configured having arc shapes that gradually widen as the outer cover 30 progresses from the one end portion 30a toward the other end portion 30b.

Figure 16:
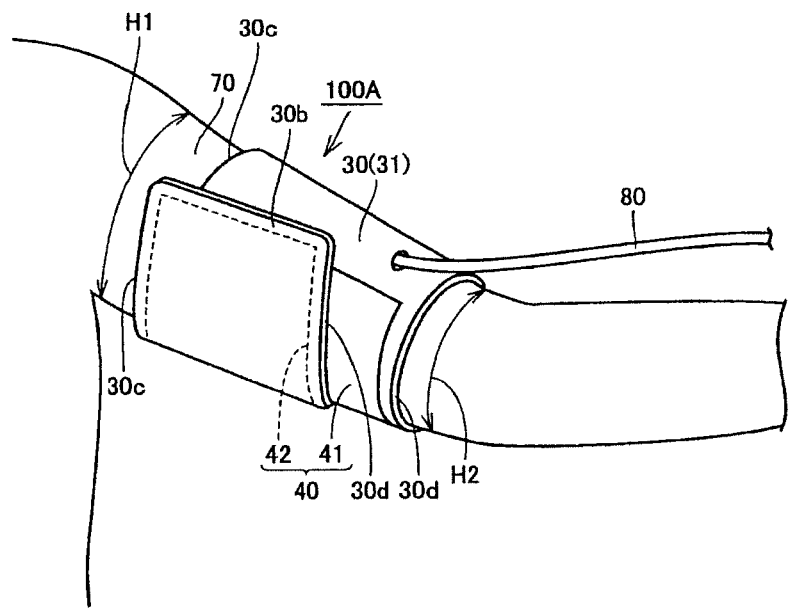
FIG. 16 is a diagram illustrating a typical cuff secured to an upper arm.
Figure 17:
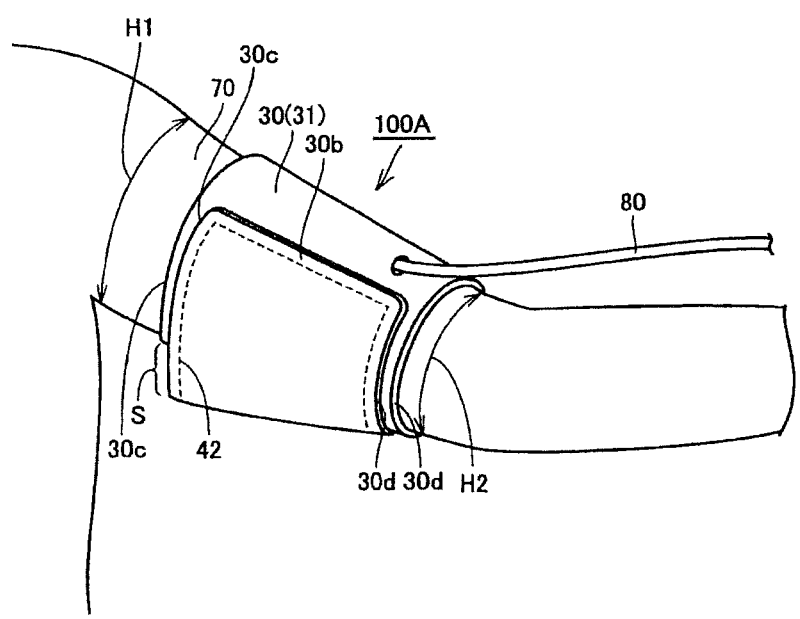
FIG. 17 is a diagram illustrating another typical cuff secured to an upper arm.

Here, assume that when the cuff 21 is wrapped around the upper arm in a ring shape, the side portion 30d side of the outer cover 30 is positioned in the vicinity of the elbow (see FIG. 16). In this case, the stated arc shape configuration of the outer cover 30 can be used while the cuff 21 is being wrapped around the upper arm. Specifically, of the side portion 30d in the outer cover 30, the side portion 30d that is not yet wrapped around the upper arm can be overlapped along the top of the side portion 30d that is already wrapped around the upper arm.

Because the side portion 30d overlaps as a whole, the side portion 30d forms a single circle around the upper arm on essentially the same plane. A sphygmomanometer provided with the cuff 21 can visually give the user a sense of stability.

Second Variation

Figure 6:
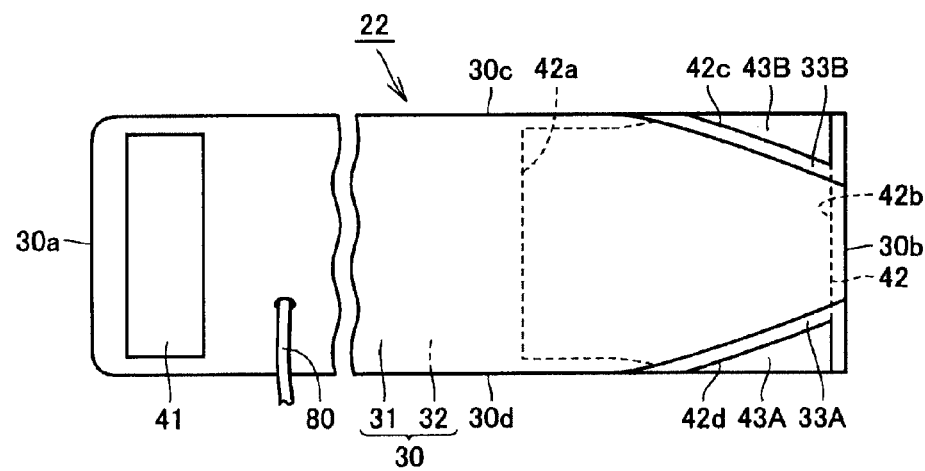
FIG. 6 is a plan view illustrating a cuff according to a second variation on the first embodiment.

A sphygmomanometer according to a second variation on the first embodiment will be described with reference to FIG. 6. In the present variation, based on the first variation on the first embodiment (FIG. 5), only the differences from the first variation will be described. The first variation and the present variation differ in that the cuff has a different configuration; the other configurations are essentially the same.

To be more specific, the first variation and the present variation differ in terms of the outer cover 30 that partially configures a cuff 22 (see FIG. 6) and the surface fastener 42 that partially configures the cuff 22.

The outer cover 30 that partially configures the cuff 22 according to the present variation has a configuration that makes it possible for the first wide portion 33A and the first wide portion 33B, respectively, to be bent back toward the front surface 31 or the rear surface 32.

Like the outer cover 30, the surface fastener 42 that partially configures the cuff 22 according to the present variation also has a configuration that makes it possible for the second wide portion 43A and the second wide portion 43B, respectively, to be bent back toward the front surface 31 or the rear surface 32.

With a configuration in which the first wide portion 33A, the first wide portion 33B, the second wide portion 43A, and the second wide portion 43B can be bent back, when a sphygmomanometer provided with the cuff 22 is stored in a case for such storage, that case can be configured having a small size. Furthermore, the stated wide portions 33A, 33B, 43A, and 43B can be suppressed from interfering with the body during the measurement of blood pressure values.

Third Variation

Figure 7:
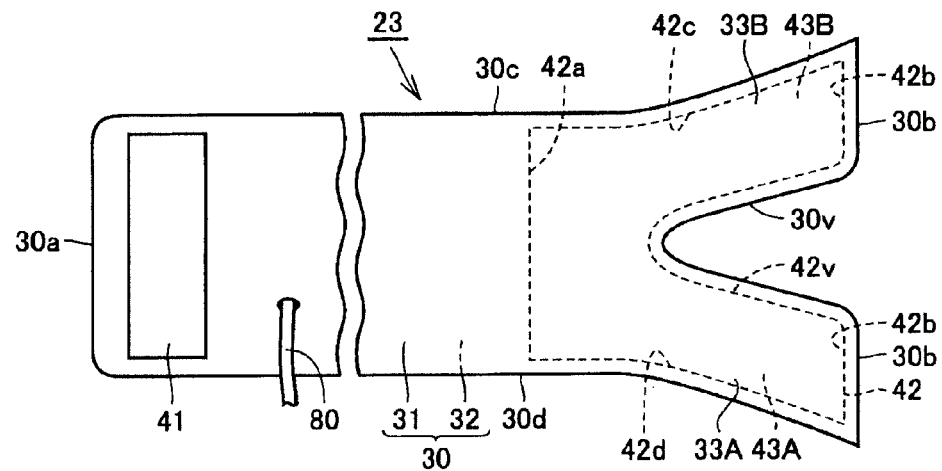
FIG. 7 is a plan view illustrating a cuff according to a third variation on the first embodiment.

A sphygmomanometer according to a third variation on the first embodiment will be described with reference to FIG. 7. In the present variation, based on the first variation on the first embodiment (FIG. 5), only the differences from the first variation will be described. The first variation and the present variation differ in that the cuff has a different configuration; the other configurations are essentially the same.

To be more specific, the first variation and the present variation differ in terms of the outer cover 30 that partially configures a cuff 23 (see FIG. 7) and the surface fastener 42 that partially configures the cuff 23.

Of the outer cover 30 that partially configures the cuff 23 according to the present variation, a cutout 30v that is approximately V-shaped from the other end portion 30b side of the outer cover 30 toward the one end portion 30a side is provided in an area that includes a region in which the surface fastener 42 is provided. The cutout 30v is positioned in approximately the center of the width direction of the outer cover 30. The cutout 30v is provided from the other end portion 30b side of the outer cover 30 toward the one end portion 30a side.

A cutout 42v that is approximately V-shaped is also provided in the surface fastener 42 that partially configures the cuff 23 according to the present variation, from the other end portion 42b side toward the one end portion 42a side. The cutout 42v is positioned in approximately the center of the width direction of the surface fastener 42, and is provided from the other end portion 42b side toward the one end portion 42a side.

Here, there are cases where after the cuff 21 according to the first variation (FIG. 5) is wrapped around the body, such as the upper arm, in a ring shape, wrinkles appear in the width direction on the other end portion 30b side of the outer cover 30 when the surface fastener 41 and the surface fastener 42 are fastened to each other. With the cuff 23 according to the present variation, the cutout 30v and the cutout 42v are provided, and thus it is possible to suppress the appearance of wrinkles in the width direction on the other end portion 30b side of the outer cover 30.

Fourth Variation

Figure 8:
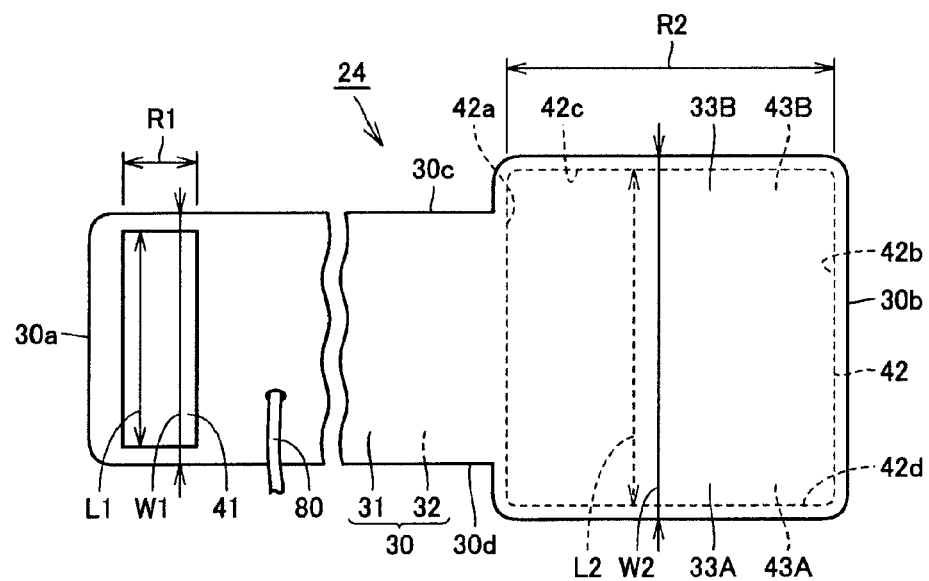
FIG. 8 is a plan view illustrating a cuff according to a fourth variation on the first embodiment.

A sphygmomanometer according to a fourth variation on the first embodiment will be described with reference to FIG. 8. In the present variation, based on the first variation on the first embodiment (FIG. 5), only the differences from the first variation will be described. The first variation and the present variation differ in that the cuff has a different configuration; the other configurations are essentially the same.

To be more specific, the first variation and the present variation differ in terms of the external shape of the outer cover 30 that partially configures a cuff 24 (see FIG. 8) and the external shape of the surface fastener 42 that partially configures the cuff 24.

In the present variation, of the outer cover 30, an area including the region R1 in which the surface fastener 41 is provided is configured as an approximate band-shape that extends in the lengthwise direction, in the same manner as in the first variation. This area has a width W1.

Of the outer cover 30 according to the present variation, the external shape of an area that includes the region R2 in which the surface fastener 42 is provided is configured as an approximately rectangular shape in which the four corners extend outward in a rounded manner.

Of the outer cover 30, the area including the region R2 in which the surface fastener 42 is provided has, in a part thereof, a width W2, in the same manner as in the first variation.

The width W2 of part of the area including the region R2 in which the surface fastener 42 is provided is, as in the first variation, set to be greater than the width W1 of the area of the outer cover 30 including the region R1. In the area of the outer cover 30 that is set to be wider, the outer cover 30 has the first wide portion 33A that protrudes toward the other side portion 30d and the other first wide portion 33B that protrudes toward the one side portion 30c.

The external shape of the surface fastener 42 according to the present variation is configured as an approximately rectangular shape in which the four corners extend outward in a rounded manner. The surface fastener 42 has, as in the first variation, a width L2 in one part thereof.

The width L2 in a part of the surface fastener 42 is, as in the first variation, set to be greater than the width L1 of the surface fastener 41. In the area of the surface fastener 42 that is set to be wider, the surface fastener 42 has the second wide portion 43A that protrudes toward the other side portion 42d and the other second wide portion 43B that protrudes toward the one side portion 42c.

As with the first variation, with the cuff 24 according to the present variation, the first wide portions 33A and 33B are provided in the outer cover 30, and the second wide portions 43A and 43B are provided in the surface fastener 42. Even in the case where the cuff 24 has been fastened with the other end portion 30 of the outer cover 30 shifted toward the shoulder, the surface fastener 41 and the surface fastener 42 can make contact with each other with a sufficient contact surface area.

Therefore, according to the cuff 24 and a sphygmomanometer provided therewith in the present variation, the cuff can be affixed to the measurement area with certainty, eliminating variations in the measurement values, which makes it possible to measure the blood pressure information in an accurate and stable manner. A sphygmomanometer provided with the cuff 24 according to the present variation can be wrapped and used on either arm (the right arm or the left arm).

Fifth Variation

Figure 9:
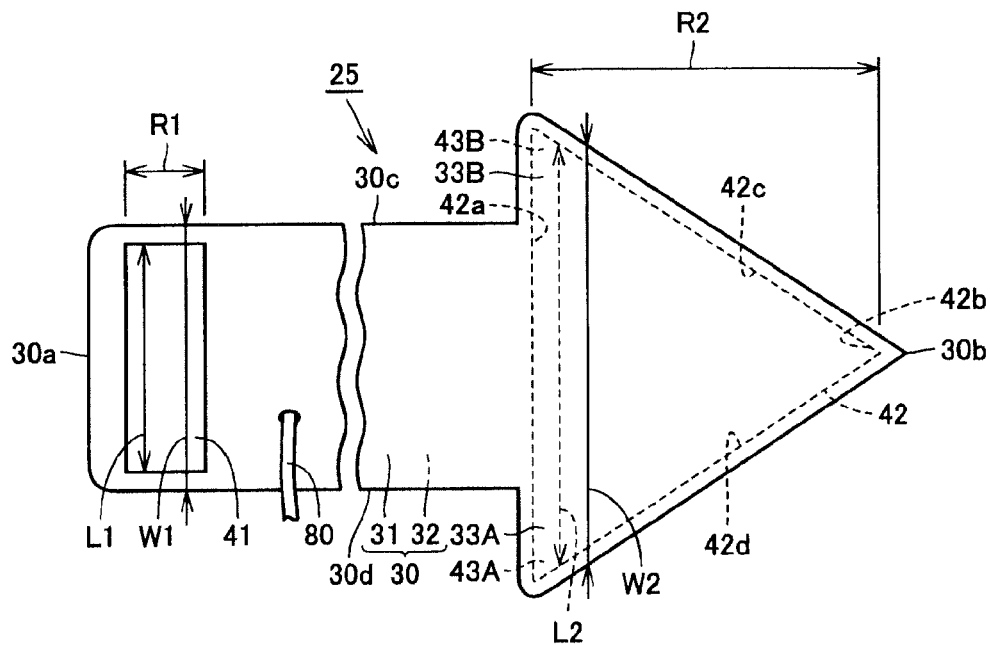
FIG. 9 is a plan view illustrating a cuff according to a fifth variation on the first embodiment.

A sphygmomanometer according to a fifth variation on the first embodiment will be described with reference to FIG. 9. In the present variation, based on the first variation on the first embodiment (FIG. 5), only the differences from the first variation will be described. The first variation and the present variation differ in that the cuff has a different configuration; the other configurations are essentially the same.

To be more specific, the first variation and the present variation differ in terms of the external shape of the outer cover 30 that partially configures a cuff 25 (see FIG. 9) and the external shape of the surface fastener 42 that partially configures the cuff 25.

In the present variation, of the outer cover 30, an area including the region R1 in which the surface fastener 41 is provided is configured as an approximate band-shape that extends in the lengthwise direction, in the same manner as in the first variation. This area has a width W1.

Of the outer cover 30 according to the present variation, an area including the region R2 in which the surface fastener 42 is provided is configured having an approximately isosceles triangular shape whose base side is located on the side of the one end portion 30a of the outer cover 30.

Of the outer cover 30, the area including the region R2 in which the surface fastener 42 is provided has, in a part thereof, a width W2, in the same manner as in the first variation.

The width W2 of part of the area including the region R2 in which the surface fastener 42 is provided is, as in the first variation, set to be greater than the width W1 of the area of the outer cover 30 including the region R1. In the area of the outer cover 30 that is set to be wider, the outer cover 30 has the first wide portion 33A that protrudes toward the other side portion 30d and the other first wide portion 33B that protrudes toward the one side portion 30c.

The surface fastener 42 according to the present variation is configured having an approximately isosceles triangular shape whose base side is located on the side of the one end portion 42a of the surface fastener 42. The surface fastener 42 has, in the same manner as in the first variation, a width L2 in one part thereof.

The width L2 in a part of the surface fastener 42 is, as in the first variation, set to be greater than the width L1 of the surface fastener 41. In the area of the surface fastener 42 that is set to be wider, the surface fastener 42 has the second wide portion 43A that protrudes toward the other side portion 42d and the other second wide portion 43B that protrudes toward the one side portion 42c.

As with the first variation, with the cuff 25 according to the present variation, the first wide portions 33A and 33B are provided in the outer cover 30, and the second wide portions 43A and 43B are provided in the surface fastener 42. Even in the case where the cuff 24 has been fastened with the other end portion 30b of the outer cover 30 shifted toward the shoulder, the surface fastener 41 and the surface fastener 42 can make contact with each other with a sufficient contact surface area.

Therefore, according to the cuff 25 and a sphygmomanometer provided therewith in the present variation, the cuff can be affixed to the measurement area with certainty, eliminating variations in the measurement values, which makes it possible to measure the blood pressure information in an accurate and stable manner. A sphygmomanometer provided with the cuff 25 according to the present variation can be wrapped and used on either arm (the right arm or the left arm).

Sixth Variation

Figure 10:
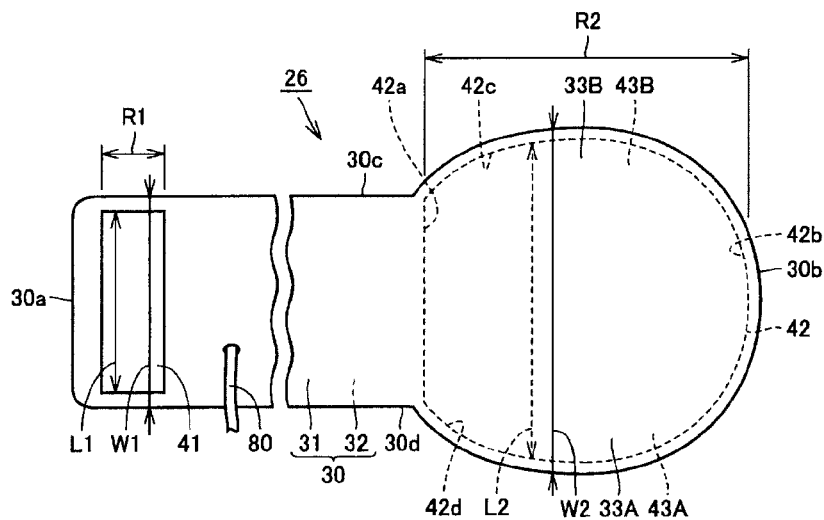
FIG. 10 is a plan view illustrating a cuff according to a sixth variation on the first embodiment.

A sphygmomanometer according to a sixth variation on the first embodiment will be described with reference to FIG. 10. In the present variation, based on the first variation on the first embodiment (FIG. 5), only the differences from the first variation will be described. The first variation and the present variation differ in that the cuff has a different configuration; the other configurations are essentially the same.

To be more specific, the first variation and the present variation differ in terms of the external shape of the outer cover 30 that partially configures a cuff 26 (see FIG. 10) and the external shape of the surface fastener 42 that partially configures the cuff 26.

In the present variation, of the outer cover 30, an area including the region R1 in which the surface fastener 41 is provided is configured as an approximate band-shape that extends in the lengthwise direction, in the same manner as in the first variation. This area has a width W1.

Of the outer cover 30 according to the present variation, an area including the region R2 in which the surface fastener 42 is provided is configured in a linear shape that is parallel to the width direction in an area on the one end portion 30a side, and is configured having an approximately elliptical shape in the other areas, continuing from the one end portion 30a side toward the other end portion 30b.

Of the outer cover 30, the area including the region R2 in which the surface fastener 42 is provided has, in a part thereof, a width W2, in the same manner as in the first variation.

The width W2 of part of the area including the region R2 in which the surface fastener 42 is provided is, as in the first variation, set to be greater than the width W1 of the area of the outer cover 30 including the region R1. In the area of the outer cover 30 that is set to be wider, the outer cover 30 has the first wide portion 33A that protrudes toward the other side portion 30d and the other first wide portion 33B that protrudes toward the one side portion 30c.

The surface fastener 42 according to the present variation is configured in a linear shape that is parallel to the width direction in an area on the one end portion 42a side of the surface fastener 42, and is configured having an approximately elliptical shape in the other areas, continuing from the one end portion 42a side toward the other end portion 42b. The surface fastener 42 has, in the same manner as in the first variation, a width L2 in one part thereof.

The width L2 in a part of the surface fastener 42 is, as in the first variation, set to be greater than the width L1 of the surface fastener 41. In the area of the surface fastener 42 that is set to be wider, the surface fastener 42 has the second wide portion 43A that protrudes toward the other side portion 42d and the other second wide portion 43B that protrudes toward the one side portion 42c.

As with the first variation, with the cuff 26 according to the present variation, the first wide portions 33A and 33B are provided in the outer cover 30, and the second wide portions 43A and 43B are provided in the surface fastener 42. Even in the case where the cuff 24 has been fastened with the other end portion 30b of the outer cover 30 shifted toward the shoulder, the surface fastener 41 and the surface fastener 42 can make contact with each other with a sufficient contact surface area.

Therefore, according to the cuff 26 and a sphygmomanometer provided therewith in the present variation, the cuff can be affixed to the measurement area with certainty, eliminating variations in the measurement values, which makes it possible to measure the blood pressure information in an accurate and stable manner. A sphygmomanometer provided with the cuff 26 according to the present variation can be wrapped and used on either arm (the right arm or the left arm).

Seventh Variation

Figure 11:
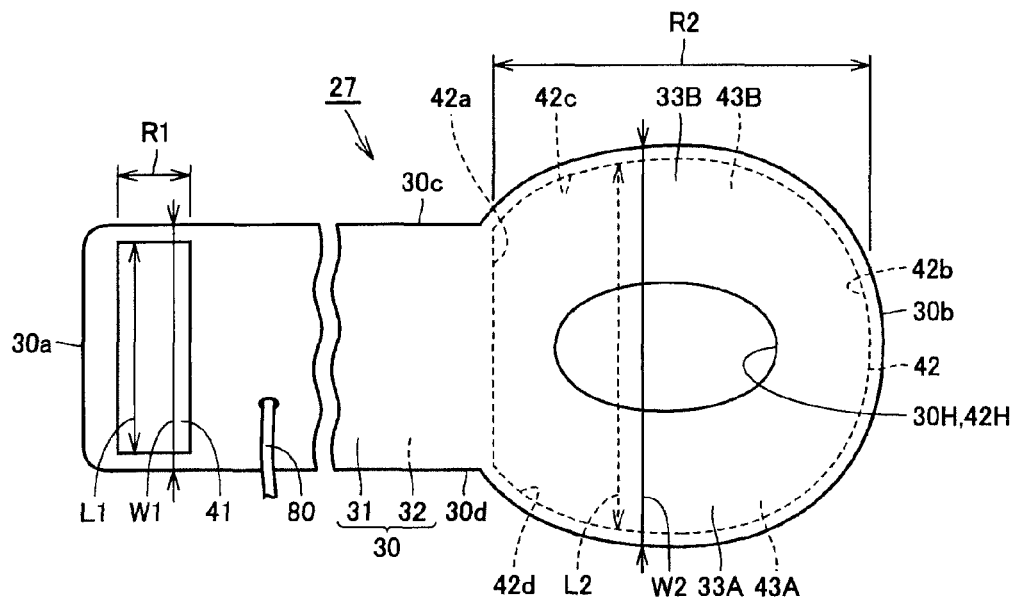
FIG. 11 is a plan view illustrating a cuff according to a seventh variation on the first embodiment.

A sphygmomanometer according to a seventh variation on the first embodiment will be described with reference to FIG. 11. In the present variation, based on the sixth variation on the first embodiment (FIG. 10), only the differences from the sixth variation will be described. The sixth variation and the present variation differ in that the cuff has a different configuration; the other configurations are essentially the same.

To be more specific, the sixth variation and the present variation differ in terms of the shape of the outer cover 30 that partially configures a cuff 27 (see FIG. 11) and the shape of the surface fastener 42 that partially configures the cuff 27.

Of the outer cover 30 that partially configures the cuff 27 according to the present variation, an opening 30H that passes through from the front surface 31 side to the rear surface 32 side is provided in an area that includes the region in which the surface fastener 42 is provided.

An opening 42H that passes through from the front surface 31 side to the rear surface 32 side is also provided in the surface fastener 42 that partially configures the cuff 27 according to the present variation.

The opening 30H in the outer cover 30 and the opening 42H in the surface fastener 42 have approximately the same shape and are disposed in approximately the same position when seen from above.

Specifically, the opening 42H and the opening 30H are formed as approximately elliptical shapes that extend in the lengthwise direction. The opening 30H and the opening 42H are located in approximately the center of the width direction and approximately the center of the lengthwise direction of the surface fastener 42.

By providing the opening 30H in the outer cover 30 and the opening 42H in the surface fastener 42, the outer cover 30 and the surface fastener 42 can easily be stretched and compressed in the lengthwise direction. Using this stretching and compression, the cuff 27 can be wrapped around a variety of body types in a flexible manner.

Second Embodiment

Figure 12:
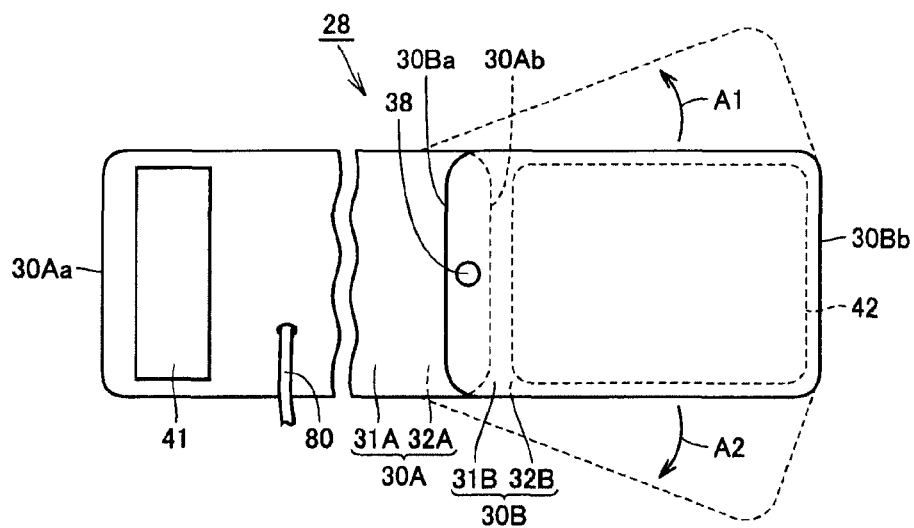
FIG. 12 is a plan view illustrating a cuff according to a second embodiment.

A sphygmomanometer according to the present embodiment will be described with reference to FIG. 12. In the present embodiment, based on the first embodiment, only the differences from the first embodiment will be described. The first embodiment and the present embodiment differ in that the cuff has a different configuration; the other configurations are essentially the same.

To be more specific, a cuff 28 according to the present embodiment (see FIG. 12) includes a first outer cover 30A, a second outer cover 30B, an air bladder (not shown) contained in the first outer cover 30A as a fluid bladder, the surface fastener 41 (first fastening member), the surface fastener 42 (second fastening member), and a connecting member 38.

The first outer cover 30A includes a front surface 31A, a rear surface 32A, a one end portion 30Aa, and another end portion 30Ab. The first outer cover 30A is formed in an approximate band shape that extends in the lengthwise direction. The air bladder is, as mentioned above, contained in the first outer cover 30A. The air bladder is connected to the air tube 80.

The surface fastener 41 is provided upon the front surface 31A of the first outer cover 30A in an approximately rectangular shape. The surface fastener 41 is provided toward the one end portion 30Aa of the first outer cover 30A. The surface fastener 41 is provided in approximately the central position of the width direction of the first outer cover 30A.

The second outer cover 30B includes a front surface 31B, a rear surface 32B, one end portion 30Ba, and another end portion 30Bb. The second outer cover 30B is formed in an approximate band shape that extends in the lengthwise direction.

The surface fastener 42 is provided upon the rear surface 32B of the second outer cover 30B in an approximately rectangular shape, so as to cover approximately the whole surface of the rear surface 32B.

The connecting member 38 connects the other end portion 30Ab side of the first outer cover 30A to the one end portion 30Ba of the second outer cover 30B in a pivotable manner. Through the connecting member 38, the second outer cover 30B can pivot relative to the first outer cover 30A in the direction indicated by an arrow A1 and the direction indicated by an arrow A2.

The connecting member 38 is formed in, for example, a cylindrical shape that extends in the vertical direction in the drawings. It is favorable for flange-shaped protrusions that extend in the cylinder radial direction to be provided in both ends (in the vertical direction in the drawings) of the connecting member 38 in order to maintain the connection between the first outer cover 30A and the second outer cover 30B.

When measuring a blood pressure value using the sphygmomanometer having the stated configuration, the cuff 28 is positioned so that the rear surface 32A of the first outer cover 30A (and the rear surface 32B of the second outer cover 30B) are opposed to the body such as the upper arm. The first and second outer covers 30A and 30B are wrapped around the upper arm in a ring shape.

The surface fastener 41 and the surface fastener 42 are fastened to each other by overlapping, thus holding the wrapped first and second outer covers 30A and 30B on the upper arm in a secured state. The air bladder is thus anchored to the body, and the blood pressure information can then be measured.

Effects

There are cases where when the cuff 28 is wrapped around the body such as the upper arm, the cuff 28 is fastened with the other end portion 30Bb of the second outer cover 30B shifted toward the shoulder.

With the sphygmomanometer according to the present embodiment, the first outer cover 30A and the second outer cover 30B are connected in a pivotable state. For example, in the aforementioned FIG. 16, the area of the surface fastener 41 that does not make contact with the surface fastener 42 and is thus exposed is covered by the surface fastener 42 as a result of the second outer cover 30B pivoting.

The surface fastener 41 and the surface fastener 42 make contact with each other with a sufficient contact surface area. By increasing the contact surface area between the surface fastener 41 and the surface fastener 42, it is possible to ensure a sufficient fastening force between the surface fastener 41 and the surface fastener 42.

The air bladder can then be inflated and deflated to the desired pressure, which makes it possible to prevent the cuff 28 from falling off the body, such as the upper arm, while the blood pressure value is being measured. Therefore, according to the cuff 28 and a sphygmomanometer provided therewith in the present embodiment, the cuff can be affixed to the measurement area with certainty, eliminating variations in the measurement values, which makes it possible to measure the blood pressure information in an accurate and stable manner.

With the sphygmomanometer according to the present embodiment, the first outer cover 30A and the second outer cover 30B are connected so as to be capable of pivoting in the directions indicated by the arrow A1 and the arrow A2. Accordingly, the sphygmomanometer provided with the cuff 28 according to the present embodiment can ensure a sufficient fastening force between the surface fastener 41 and the surface fastener 42 by causing the second outer cover 30B to pivot, regardless of which arm (the right arm or the left arm) the cuff 28 is wrapped around and used.

Third Embodiment

Figure 13:
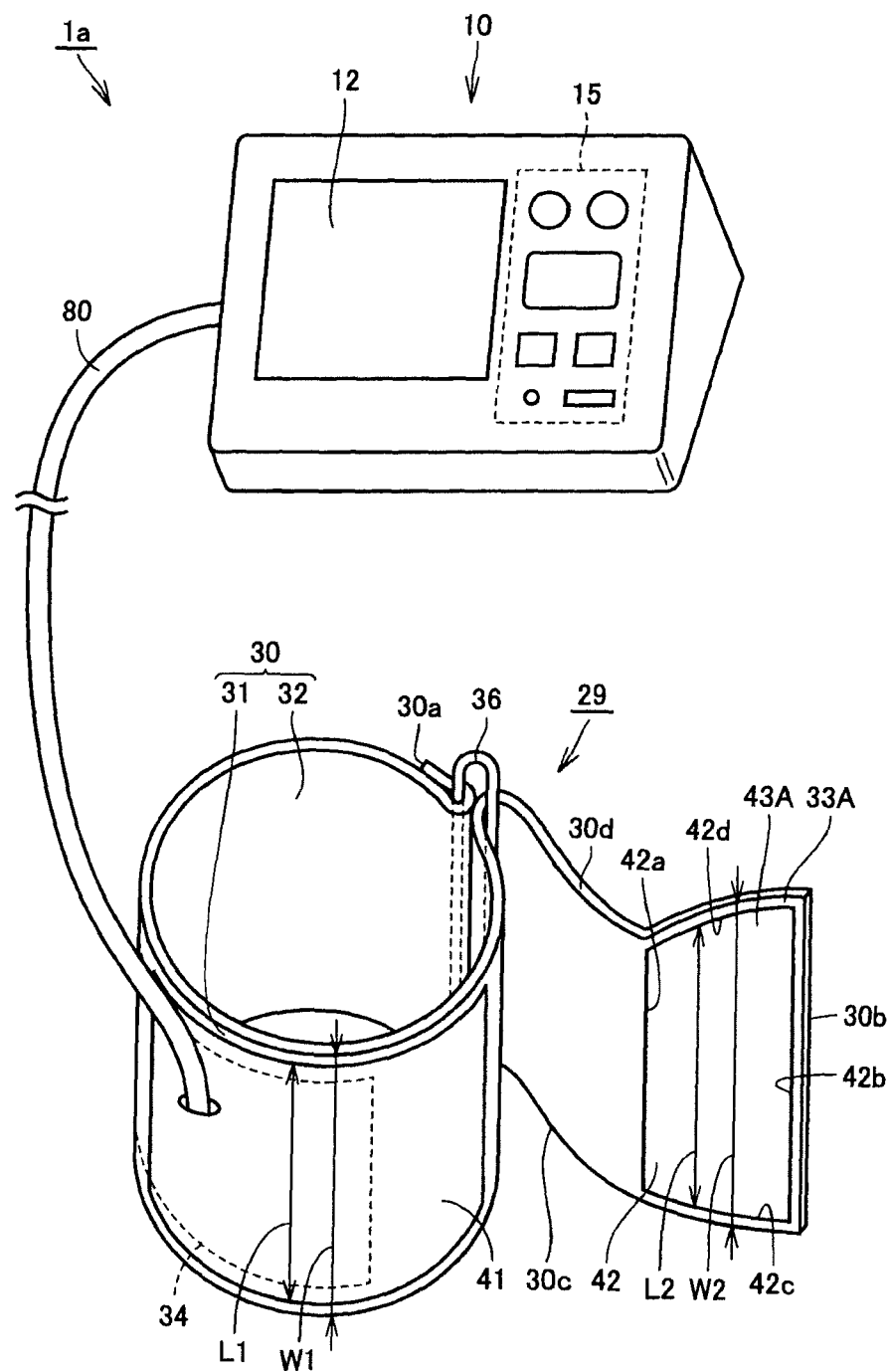
FIG. 13 is a diagram illustrating the overall configuration of a sphygmomanometer according to a third embodiment.
Figure 14:
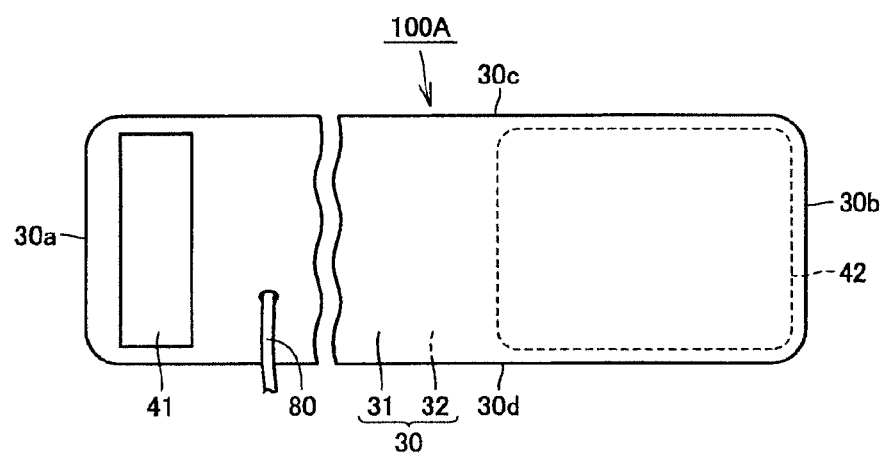
FIG. 14 is a plan view illustrating a typical cuff.
Figure 15:
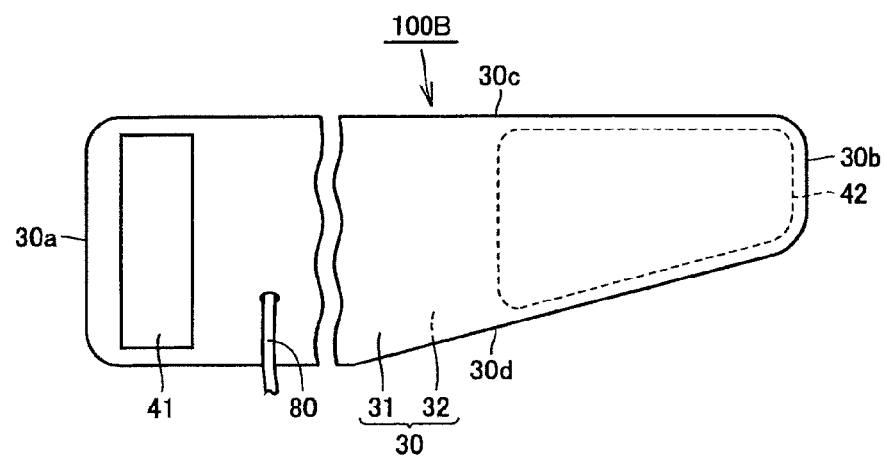
FIG. 15 is a plan view illustrating another typical cuff.

A sphygmomanometer 1a according to a third embodiment will be described with reference to FIG. 13. In the present embodiment, only the differences from the first embodiment will be described. The first embodiment and the present embodiment differ in that the cuff has a different configuration; the other configurations are essentially the same.

To be more specific, a cuff 29 according to the present embodiment (see FIG. 13) includes the outer cover 30, the air bladder 34 contained in the outer cover 30 as a fluid bladder, the surface fastener 41 (first fastening member), the surface fastener 42 (second fastening member), and a circular ring 36.

The one side portion 30c of the outer cover 30 is configured in an approximately linear shape following the lengthwise direction. Of the outer cover 30, an area including a region in which the surface fastener 41 is provided is configured as an approximate band-shape that extends in the lengthwise direction. This area has a width W1.

In the outer cover 30, only the other side portion 30d is configured so as to curve outward (upward, in the drawings) and widen. The other side portion 30d of the outer cover 30 is configured so that the width of the outer cover 30 gradually increases in an area of the outer cover 30 that includes a region in which the surface fastener 42 is provided, as the outer cover 30 progresses from the one end portion 30a toward the other end portion 30b.

Of the outer cover 30, the area including the region in which the surface fastener 42 is provided has, in a part thereof, a width W2.

The width W2 of part of the area including the region in which the surface fastener 42 is provided is set to be greater than the width W1 of the area of the outer cover 30 including the region in which the surface fastener 41 is provided. In the area of the outer cover 30 that is set to be wider, the outer cover 30 has a first wide portion 33A that protrudes toward the other side portion 30d.

The surface fastener 41 is provided upon the front surface 31 of the outer cover 30 in an approximately rectangular shape. The surface fastener 41 is provided between the one end portion 30a and the other end portion 30b of the outer cover 30 in the lengthwise direction thereof. The surface fastener 41 is provided in approximately the central position of the width direction of the outer cover 30. The surface fastener 41 has a width L1.

The surface fastener 42 is, like the surface fastener 41, provided upon the front surface 31 of the outer cover 30. The surface fastener 42 is provided toward the other end portion 30b of the outer cover 30. The surface fastener 42 has one end portion 42a, another end portion 42b, one side portion 42c, and another side portion 42d.

The one side portion 42c of the surface fastener 42 is configured in a linear shape that is approximately parallel to the lengthwise direction of the outer cover 30.

In the surface fastener 42, only the other side portion 42d is configured so as to curve outward (upward, in the drawings) and widen. The other side portion 42d of the surface fastener 42 is configured so that the width of the surface fastener 42 gradually increases as the surface fastener 42 progresses from the one end portion 42a toward the other end portion 42b. The surface fastener 42 has a width L2 in a part thereof.

The width L2 in a part of the surface fastener 42 is set to be greater than the width L1 of the surface fastener 41. In the area of the surface fastener 42 that is set to be wider, the surface fastener 42 has a second wide portion 43A that protrudes toward the other side portion 42d.

The circular ring 36 is attached on the one end portion 30a side of the outer cover 30. The circular ring 36 is attached to the outer cover 30 by passing an area of the outer cover 30 on the one end portion 30a side through the circular ring 36, bending that area back, and stitching that area.

The circular ring 36 is configured of, for example, a metallic member that is unlikely to produce friction with the outer cover 30, and has an insertion hole through which an area of the outer cover 30 on the other end portion 30b side can be passed. The outer cover 30 is held in a ring shape by passing the other end portion 30b of the outer cover 30 through the insertion hole of the circular ring 36 attached near the one end portion 30a of the outer cover 30.

The area of the outer cover 30 on the other end portion 30b side is bent back, central to the circular ring 36, toward the circular ring 36 and along the circumferential direction of the area of the outer cover 30 formed in a ring shape.

When measuring a blood pressure value using the sphygmomanometer 1a having the stated configuration, for example, the upper-left arm (not shown) of the measurement subject is inserted into the outer cover 30 that has been formed into a ring shape. The outer cover 30 is secured to the upper arm by the measurement subject using his or her right hand to pull the other end portion 30b of the outer cover 30 in the direction away from the circular ring 36.

By being fastened to each other, the surface fastener 41 and the surface fastener 42 maintain a state in which the wrapped outer cover 30 is secured to the upper arm. The air bladder contained within the outer cover 30 is thus anchored to the upper arm, and the blood pressure information can then be measured.

In the sphygmomanometer 1a according to the present embodiment, the first wide portion 33A is provided in the outer cover 30, and the second wide portion 43A is provided in the surface fastener 42. In addition, in the sphygmomanometer 1a according to the present embodiment, the side portion on which the first wide portion 33A and the second wide portion 43A are provided (the other side portion 30d) is disposed so as to be positioned toward the elbow.

When the cuff 29 is wrapped around a body such as the upper arm, there are cases where the cuff 29 is fastened in a state where the side portion 30c in the other end portion 30b of the outer cover 30 is shifted toward the shoulder. With the sphygmomanometer 1a according to the present embodiment, the second wide portion 43A is provided in the surface fastener 42, and thus the surface fastener 41 and the surface fastener 42 make contact with each other with a sufficient contact surface area. By increasing the contact surface area between the surface fastener 41 and the surface fastener 42, it is possible to ensure a sufficient fastening force between the surface fastener 41 and the surface fastener 42.

The air bladder 34 can then be inflated and deflated to the desired pressure, which makes it possible to prevent the cuff 29 from falling off the body, such as the upper arm, while the blood pressure value is being measured. Therefore, according to the cuff 29 and the sphygmomanometer 1a provided therewith in the present embodiment, the cuff can be affixed to the measurement area with certainty, eliminating variations in the measurement values, which makes it possible to measure the blood pressure information in an accurate and stable manner.

According to one or more embodiments of the present invention, the configurations (technical spirit) of the first embodiment (including the first through seventh variations; the same applies hereinafter) and the third embodiment can be combined as appropriate. The configurations (technical spirit) of the second embodiment and third embodiment can also be combined as appropriate.

Although the first through third embodiments describe, as an example, a so-called upper arm-type sphygmomanometer in which the cuff is affixed to the upper arm when measuring a blood pressure value, and a sphygmomanometer cuff provided therein, one or more embodiments of the present invention are not particularly limited thereto.

According to one or more embodiments of the present invention, the configurations of the first through third embodiments can also be applied in a so-called wrist-type sphygmomanometer in which the cuff is affixed to the wrist when measuring a blood pressure value, and a sphygmomanometer cuff provided therein.

The configurations of the first through third embodiments can also be applied in a so-called ankle-type sphygmomanometer in which the cuff is affixed to the ankle when measuring a blood pressure value, and a sphygmomanometer cuff provided therein.

Although the first through third embodiments describe examples in which the configurations are applied in a sphygmomanometer capable of measuring a systolic blood pressure value, a diastolic blood pressure value, and so on, and in a sphygmomanometer cuff provided therein, one or more embodiments of the present invention are not particularly limited thereto.

The configurations of the first through third embodiments can also be applied in a blood pressure information measurement device capable of measuring other blood pressure information aside from blood pressure values such as a systolic blood pressure value and a diastolic blood pressure value (for example, an average blood pressure value, a sphygmogram, a pulse, an AI (augmentation index) value, and so on), and in a blood pressure information measurement device cuff provided therein.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

REFERENCE NUMERALS LIST 1, 1a sphygmomanometer
10 main body
11 control unit
12 display unit
13 memory unit
13a processing memory
13b data memory
14 power supply unit
15 operating unit
15a power switch
15b measurement switch
15c stop switch
15d record call switch
16 air system component
16a pressure pump
16b exhaust valve
16c pressure sensor
17a pressure pump driving circuit
17b exhaust valve driving circuit
17c oscillation circuit
20-29, 100A, 100B cuff
30, 30A, 30B outer cover
30a, 30Aa, 30Ba, 42a one end portion
30Ab, 30b, 30Bb, 42b other end portion
30c, 30d, 42c, 42d side portion
30H, 42H opening
31, 31A, 31B front surface
32, 32A, 32B rear surface
33A, 33B first wide portion
34 air bladder
36 circular ring
38 connecting member
41, 42 surface fastener
43A, 43B second wide portion
70 upper arm
80 air tube
A1, A2 arrow
L1, L2, W1, W2 width
R1, R2 region
S gap
ST1-ST13 step

The invention claimed is:

1. A blood pressure information measurement device cuff comprising:
a fluid bladder that applies pressure to a body;
an outer cover, comprising a first main surface and a second main surface, that contains the fluid bladder toward a first end portion;
a first fastening member provided toward the first end portion on the first main surface; and
a second fastening member provided toward a second end portion on the first main surface or toward the second end portion on the second main surface, wherein the outer cover is adapted to be wrapped around the body in a ring shape;
the first fastening member and the second fastening member are adapted to hold the wrapped outer cover on the body in a secured state;
the outer cover comprises, in an area of the outer cover that comprises a region in which the second fastening member is provided, a first wide portion in which the width of the outer cover is greater than a width of an area of the outer cover that comprises a region in which the first fastening member is provided; and
the second fastening member comprises a second wide portion in which the width of the second fastening member is greater than a width of the first fastening member,
wherein the second wide portion of the second fastening member is on the first wide portion of the outer cover,
wherein at least one side edge of the outer cover in the first wide portion is curved outwardly from an elongated center line of the outer cover,
wherein at least one side edge of the second fastening member in the second wide portion is curved outwardly from the elongated center line of the outer cover,
wherein the second end portion of the outer cover is wider than the width of the first end portion of the outer cover, and
wherein the second end portion of the second fastening member is wider than the width of the first end portion of the outer cover.

2. The blood pressure information measurement device cuff according to claim 1, wherein the first wide portion in the outer cover and the second wide portion in the second fastening member have approximately arc shapes in which the widths gradually increase outward in the width direction as the outer cover progresses from the first end portion toward the second end portion.

3. The blood pressure information measurement device cuff according to claim 1, wherein the first wide portion in the outer cover and the second wide portion in the second fastening member have shapes in which the widths increase outward on both sides in the width direction as the outer cover progresses from the first end portion toward the second end portion.

4. A blood pressure information measurement device comprising:
   the blood pressure information measurement device cuff according to claim 1;
   an inflation/deflation mechanism that inflates/deflates the fluid bladder; and
   a blood pressure information obtainment unit that obtains blood pressure information.

5. The blood pressure information measurement device cuff according to claim 1, wherein the width of a portion of the first wide portion of the outer cover gradually increases towards the second end portion.

6. The blood pressure information measurement device cuff according to claim 1, wherein the width of a portion of the second wide portion of the second fastening member gradually increases towards the second end portion away from the first fastening member.

\* \* \* \* \*